(12) United States Patent
Grundler et al.

(10) Patent No.: US 8,631,973 B2
(45) Date of Patent: Jan. 21, 2014

(54) SINGLE-USE CARTRIDGES FOR THE STORING AND DISPENSING OF DENTAL TWO-COMPONENT IMPRESSION MATERIALS

(75) Inventors: Andreas Grundler, Dormagen (DE); Klaus-Dieter Nehren, Dormagen (DE); Alfred von Schuckmann, Kevelaer (DE)

(73) Assignee: Heraeus Kulzer GmbH, Hanau (DE)

( * ) Notice: Subject to any disclaimer, the term of this patent is extended or adjusted under 35 U.S.C. 154(b) by 467 days.

(21) Appl. No.: 12/826,182

(22) Filed: Jun. 29, 2010

(65) Prior Publication Data

US 2010/0330525 A1 Dec. 30, 2010

(30) Foreign Application Priority Data

Jun. 30, 2009 (DE) .......................... 10 2009 031 306

(51) Int. Cl.
*B67D 7/70* (2010.01)
(52) U.S. Cl.
USPC ...... 222/137; 222/145.6; 222/168; 366/172.1
(58) Field of Classification Search
USPC ................... 222/137, 145.5, 145.6, 167, 168; 366/171.1–172.2
See application file for complete search history.

(56) References Cited

U.S. PATENT DOCUMENTS

| 3,144,966 | A | * | 8/1964 | Cook | 222/136 |
| 3,587,982 | A | * | 6/1971 | Campbell | 241/62 |
| 5,501,371 | A | * | 3/1996 | Schwartz-Feldman | 222/136 |
| 2007/0228076 | A1 | | 10/2007 | Horner | |
| 2010/0206904 | A1 | * | 8/2010 | Staub et al. | 222/137 |

FOREIGN PATENT DOCUMENTS

| DE | 3233366 A1 | 9/1983 |
| EP | 1 308 137 A2 | 5/2003 |
| WO | 2005/095225 A1 | 10/2005 |
| WO | 2006/060628 A1 | 6/2006 |
| WO | 2007/126532 A2 | 11/2007 |
| WO | 2008/048603 A2 | 4/2008 |
| WO | 2008/076941 A1 | 6/2008 |

* cited by examiner

*Primary Examiner* — Kevin P Shaver
*Assistant Examiner* — Daniel R Shearer
(74) *Attorney, Agent, or Firm* — Norris McLaughlin & Marcus, P.A.

(57) ABSTRACT

Single-use cartridges for the storing and dispensing of dental two-component impression materials have a closable external chamber with a cylinder-shaped external wall, a cylindrical closable internal chamber that is arranged coaxially or eccentric therein, a mixing element including housing and mobile mixer that is to be mounted separately or connected firmly to the external chamber at its inlet end. Either the internal cylindrical chamber is arranged such that it can be rotated and forms the drive shaft for the mobile mixer part of the mixing element, or the drive shaft extends parallel to the central axis through the internal cylindrical chamber or forms the central axis. The content of the chambers can be dispensed by means of conveying means whose axial thrust motions can be controlled independent of each other.

6 Claims, 4 Drawing Sheets

SINGLE-USE CARTRIDGES FOR THE STORING AND DISPENSING OF DENTAL TWO-COMPONENT IMPRESSION MATERIALS

BACKGROUND OF THE INVENTION (1) Field of the Invention

The invention relates to single-use cartridges for the storing and dispensing of dental two-component impression materials.

(2) Description of Related Art

Impression materials for taking dental impressions are commercially available as a combination of two components that are stored separately and mixed prior to use. The mixture hardens after a processing time on the order of minutes during which the material is filled into an impression tray at the dentist's followed by taking the impression in the mouth of the patient. The hardened impression is then removed and serves for fabrication of the model or is scanned in order to produce a virtual model.

Impression materials can be mixed in the dental office by stirring in manual mode or through the use of so-called automix devices. Mixing devices of this type for automatic mixing of dental impression materials are commercially available on the market, e.g. as models of the Pentamix® series made by 3M ESPE, Plug&Press® Dispenser made by Kettenbach, MixStar® made by DMG or Dynamix® made by Heraeus Kulzer.

There continues to be a need to improve said devices and systems with regard to their user comfort and the reliability and reproducibility of the process of taking an impression. It is desirable for the user to be able to fill impression trays easily and rapidly and to pre-select and/or vary the processing time in this context.

The inventors mainly pursued the goal to develop a system that allows impression materials to be mixed automatically by a device in the dental office and, in this context, have the processing time set variably by the user/dentist/assistant—as was previously possible only with hand-mixed and hand-dosed impression materials.

An additional requirement is the ease of handling, preferably for single use (single-use/single-dose) allowing the time needed for the entire process of preparing and filling the impression tray to be minimized. This time need includes everything that needs to be done in relation to filling the impression tray, including providing and dosing the material, assembly of components, and disposal of residual amounts as well as cleaning. In detail, these processes include the following Hand- or motor-operated devices have become established in dental offices in the past few years that dose and convey impression materials from tubular bag systems or multi-chamber cartridges and at the same time mix them by means of static or rotating attachments. For complete filling of impression trays, it is customary to use motor-operated devices that are fitted with twin-cartridges or tubular bags with a capacity of 360 to 380 ml. These package sizes last for an average of 10 tray fillings. These devices are therefore used together with replaceable rotating mixing attachments that are intended for single use. Some of these attachments are quite laborious to connect to the device and/or cartridge.

For smaller amounts (e.g. for impression taking of prepared single teeth or correctable impressions), multi-use twin-cartridges with a capacity of 25 to 75 ml and replaceable static single-use mixers are used.

WO 2007/126532 and US 2007/0228076 describe multi-component cartridges and EP 1 846 308 describes multi-component syringes that contain clearly smaller amounts of 0.5 to 2.5 ml such that this amount, with a static mixer that is screwed on or plugged on, is sufficient for a single-use application with correctable impression material.

WO 2008/048603 describes pre-filled portion packages whose content is to be mixed by hand.

EP 1 308 137 A2 presents a mixing device that facilitates variable dosing of liquid components. The subject matter of DE 32 33 366 A1 is an apparatus that triggers the plungers of two cartridges separately such that the individual components can have different dispensing speeds.

However, the systems described above are associated with the following disadvantages:

The large-volume tubular bags and cartridges require correspondingly large and powerful machines which take up much working space in the office, which frequently is not available. Replacement of the cartridges and mixers is associated with time expenditure and soiling and/or contamination by the components of the product. Once a cartridge is fitted with the components, the filling levels of the two component chambers first need to be levelled by discarding some material that is conveyed from the device.

The paste mixture that is conveyed out always has a processing time that is determined by the material, but subject to the influence of ambient and/or storage temperature. This leads to large variations of the processing times of said mixtures depending on seasonal and climatic zone influences. To correct this problem, said materials are commercially available having different processing times settings, e.g. as regular set or fast set, or it is recommended to temperature-equilibrate them in the refrigerator or temperature-controlled cabinet.

Meanwhile many different rotating mixers have become established in the market, but are not mutually compatible in many cases or do not result in an optimal mixture for the consistency at hand. The user is therefore often forced to keep in stock multiple mixers that might later be confused.

Although cartridges for dispensing by means of hand-operated devices hold a volume of 40-50 ml on average which is sufficient for complete filling of one impression tray, they necessitate the use of very much force or expenditure of very much time. Kneadable consistencies cannot be conveyed by them at all. The climate and processing time issue mentioned above applies in this case in the same manner.

In older systems, for example those of the silicone impression materials that cross-link by means of condensation polymerization, the user can use under- or overdosing of the activator to individually control the processing time since the components of said materials are provided individually in tubes, cans or bottles. Neither of the cartridge, tubular bag, and syringe systems that are commercially available thus far can provide this advantage any longer due to their fixed dosage. However, the option of variable dosing is associated with disadvantages in that said materials can be dosed incorrectly or the mixing thereof is often poor or insufficient and requires adept users.

BRIEF SUMMARY OF THE INVENTION

The objective presented above was met by a coaxial cartridge according to claim 1 and matching conveying means according to claim 5. Further developments are evident from the dependent claims.

It is expedient for the rotor of the mixer to be part of the internal part, and the stator/shell of the mixer to be part of the external shell of the cartridge.

The mixer spout can be connected firmly to the cartridge. The spout can just as well be connected to the cartridge by means of a rotating and/or plug-in motion.

The volume is expediently designed such that a sufficient amount each of the two components required for one filling of the impression tray is filled into and stored in the coaxial multi-component cartridge. This defines a single-use application and there is no time needed for leveling the component chambers or cleaning of parts.

It is advantageous for the mixing element to be connected firmly to the cartridge, or to be integrated therein.

This can be implemented by the rotating part of the mixer being an extension of the internal cartridge chamber. What is novel about this is that the entire internal chamber of the coaxial cartridge works as drive shaft for the rotating mixer, meaning that it can be rotated.

The feature of controlling the processing time is implemented by the mixing ratio of the two components. This facilitates that the two plungers of the component chambers can be conveyed at different speeds independent of each other.

This is made possible, for example, by designing a conveying piston for the external chamber to be tube-shaped and designing the internal conveying piston for the internal chamber that extends therein to be cylindrical in shape. The thrust of the conveying pistons can be controlled independently. The invention also relates to a conveying means of this type.

The variation of the processing time can be designed such that it can be set by the user by means of switch/regulator. In addition or alternatively, the dosing can be corrected on the part of the device by means of the ambient or paste temperature.

The advantages of the cartridges according to the invention, some of which are obvious, can be summarized as follows:

Since this concerns single-use applications, there is no cleaning effort at all involved.

Since the mixer is integrated, it does not need to be kept in stock separately and there is no risk of confusing mixers. The mixer does not need to be attached and fixed separately. Through expedient designing of the internal mixing chamber, it is feasible to provide an automatic cartridge opening function.

The requisite mixing device can be designed to be significantly smaller than is the case in earlier motor-operated mixing devices for tray materials. It therefore takes up significantly less space on the working surface of a treatment room.

In addition, the device can be designed to be significantly lighter-weight such that, e.g., storage battery-operated mobile variants are feasible as well. Earlier devices are too bulky and too heavy for this.

The entire handling, from the insertion of the cartridge via the filling of the impression tray to disposal is reduced to but a few seconds.

The conveying of the components being driven independently allows the processing time to be varies by means of changing the mixing ratio.

This allows the user to pre-select his/her desired processing time.

In addition, taking the ambient temperature into consideration allows for a response to the ambient temperature such that constant processing times can be implemented with this system throughout the world and at any time of the year.

The resulting application options are as follows:

Single-use cartridges for storing, dosing, and mixing of, preferably, medium-viscosity to kneadable dental impression materials as are required for filling impression trays.

Another application option exists with duplication materials for dental laboratory work.

The ease of use renders the application, e.g., in model-making, forensics, archaeology, metallography, hobby and handicraft applications conceivable.

The mixer attachment can be designed to be replaceable just as well by varying the mixer attachment. In this case, the device needed could also be used for lower consistencies at which only small amounts are required for correctable impressions or bite recording and/or the device/cartridge system would lend itself to multiple filling also.

Exemplary embodiments of the invention are depicted in the figures. In the figures:

BRIEF DESCRIPTION OF THE SEVERAL VIEWS OF THE DRAWING(S)

DETAILED DESCRIPTION OF THE INVENTION

Figure 1:
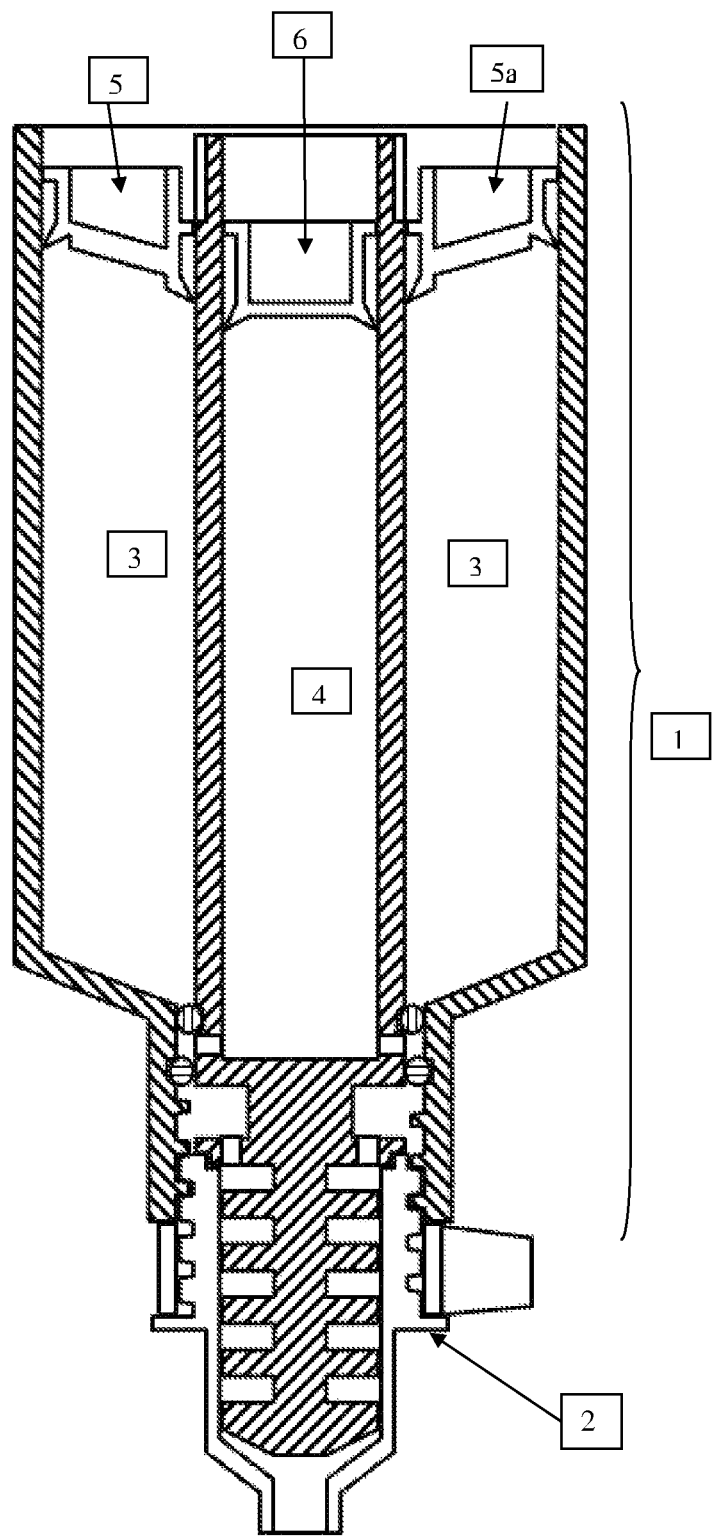
FIG. 1 shows an embodiment of the cartridge with mixer attachment.

The cartridge 1 shown in FIG. 1 comprises a mixing attachment 2. The internal chamber 4 (Cat) is arranged coaxially in the external chamber 3 (Base) in this case. The ring-shaped lid 5, 5a of the external chamber 3 can be seen in a cross-section at the end of cartridge 1 facing away from the mixing attachment. The piston 6 of the internal chamber 4, which is supported such that it can rotate about its longitudinal axis in the present case, can be fitted with a connecting means (e.g. crown wheel, Inbus®) and driven by a rod-shaped piston with an end that matches the connecting means. It can be used to affect both thrust and rotation of the internal chamber. The thrust on the ring-shaped lid 5, 5a of the external chamber 3 can be effected similarly by a tube-shaped piston.

Figure 2:
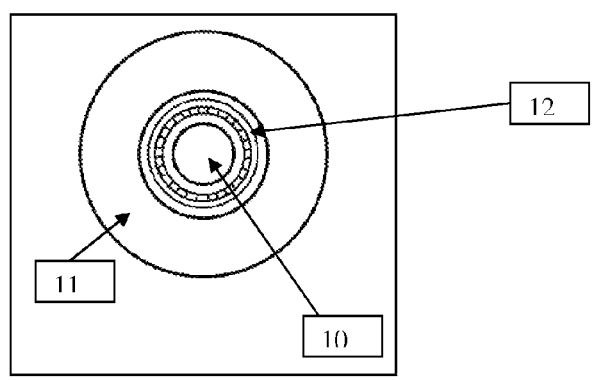
FIG. 2 shows a functional model of the arrangement of concentric drive pistons for thrust and rotation.
Figure 3:
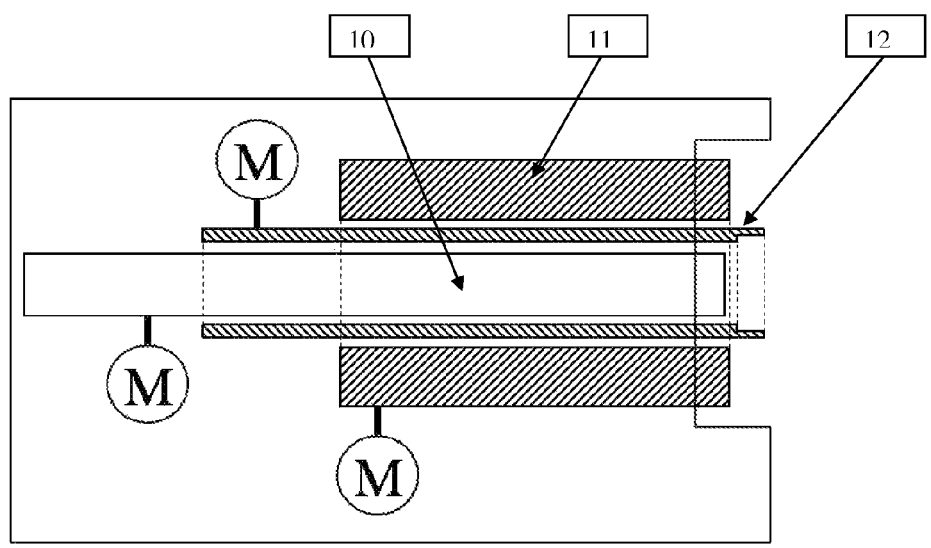
FIG. 3 shows a lateral view of the embodiment depicted in FIG. 2.

FIG. 2 and FIG. 3 show corresponding pistons 10, 11 that are arranged one inside the other.

Figure 4:
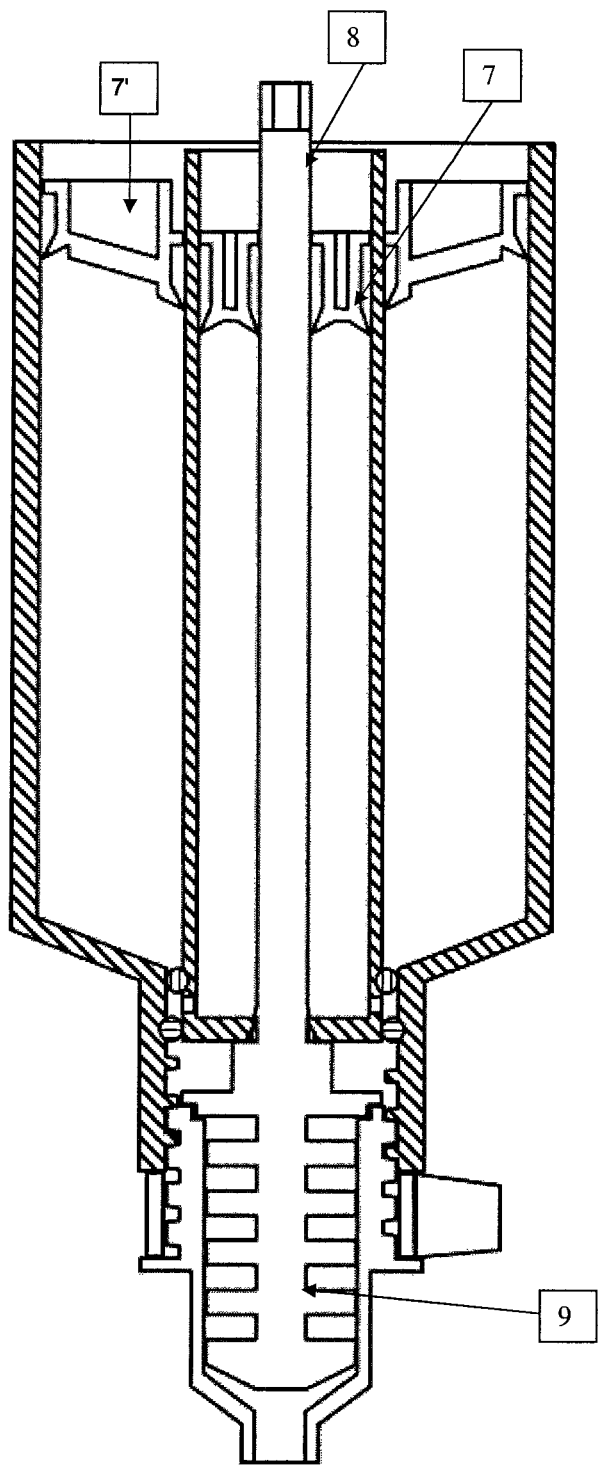
FIG. 4 shows a variant, in which the drive shaft for the mixer extends through the internal cartridge.

FIG. 4 shows a variant, in which two coaxial cylinder-shaped chambers surround a drive shaft for the mixer. The two ring pistons 7' and 7 and the drive shaft 8 and the mixing attachment 9 in their shared central axis are shown.

Figure 5:
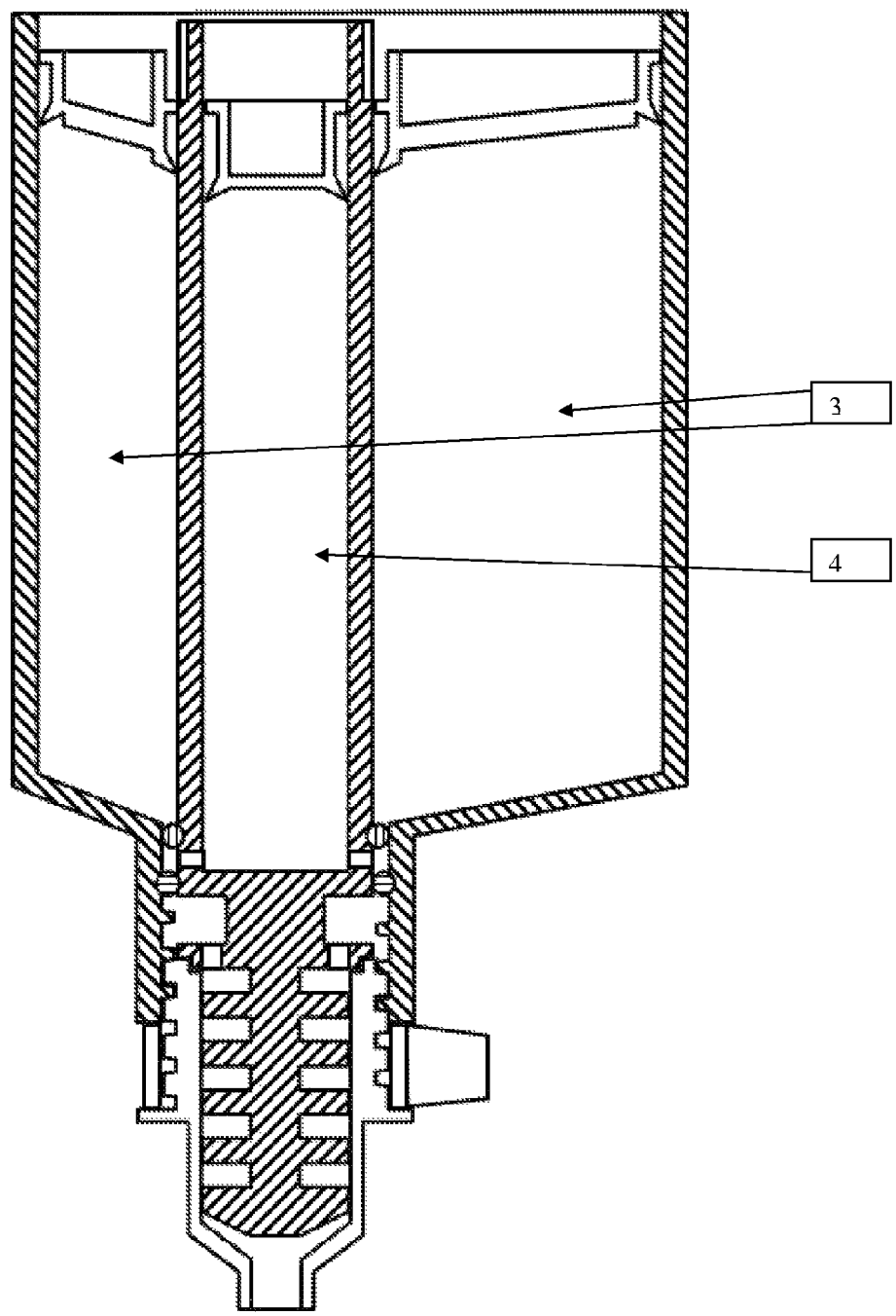
FIG. 5 shows an eccentric arrangement of the internal chamber relative the central axis of the external chamber.

FIG. 5 shows a variant with eccentric arrangement of the internal chamber 4. It is obvious that the pistons effecting thrust and rotation are to be attached with a corresponding offset.

The invention claimed is:

1. A single-use cartridge for storing and dispensing of dental two-component impression materials comprising
   (a) a closable external chamber having an outlet end and a cylindrical external wall for containing a first component;
   (b) a closable internal cylindrical chamber comprising a lid with a connecting device to close the internal cylindrical chamber, the closable internal cylindrical chamber, arranged coaxially or eccentrically in the closable external chamber for containing a second component;
   (c) a mixing element mounted detachably to the external chamber at the outlet end;

wherein the closable internal cylindrical chamber is arranged such that it is rotatable and forms a drive shaft for the mixing element and wherein the closable external chamber and the closable internal chamber each include a measured volume of component material to provide a measured amount of impression material to fill an impression tray.

2. The single-use cartridge according to claim 1, wherein the mixing element includes a mixing spout attached to the cartridge.

3. The single-use cartridge according to claim 2, wherein the attachment of the static mixing spout is accomplished by a screwing connection or by sliding.

4. The cartridge according to claim 1, wherein the connecting device is constructed in such a way that a rod shaped piston matches the connecting device.

5. A conveying device for a single-use cartridge for storing and dispensing of dental two-component impression materials comprising
   a. a closable external chamber having a cylindrical external wall and an outlet end;
   b. a cylindrical closable internal chamber, arranged coaxially or eccentric therein;
   c. a mixing element mounted to the external chamber at the outlet end;

wherein the internal cylindrical chamber is rotatably arranged and forms a drive shaft for a mobile part of the mixing element; and wherein the conveying device comprises two independent conveying pistons having axial thrust motion that are controllable independent of each other, and wherein the external chamber and the internal chamber each include a measured volume of component material to-provide a measured amount of impression material to fill an impression tray.

6. A conveying device according to claim 5, comprising a tube-shaped external conveying piston and a cylindrically rod-shaped internal conveying piston that is arranged to be coaxial or eccentric therein.

* * * * *